United States Patent [19]

Kaltenbronn et al.

[11] Patent Number: 5,221,667

[45] Date of Patent: Jun. 22, 1993

[54] RENIN INHIBITING PEPTIDES HAVING AN α-HETEROATOM AMINO ACID AT THE $P_3$ POSITION

[75] Inventors: James S. Kaltenbronn; Joseph T. Repine, both of Ann Arbor, Mich.

[73] Assignee: Warner-Lambert Company, Morris Plains, N.J.

[21] Appl. No.: 468,391

[22] Filed: Jan. 22, 1990

[51] Int. Cl.$^5$ .................... A61K 37/00; C07K 5/00
[52] U.S. Cl. ......................... 514/19; 514/18; 530/330; 530/331; 530/800
[58] Field of Search .......... 514/18, 19; 530/331, 530/330, 800

[56] References Cited

U.S. PATENT DOCUMENTS 5,036,054  7/1991  Kaltenbronn .................. 514/19

FOREIGN PATENT DOCUMENTS 202557  11/1986  European Pat. Off. .
0229667  7/1987  European Pat. Off. ............ 514/19

OTHER PUBLICATIONS

Burger, *Medicinal Chemistry*, 1960, pp. 565-571, 578-581, 600-601.
Plattner et al. *J. Med. Chem.* 1988, 31(12):2277-2288.
Bolis et al. *J. Med. Chem.* 1987, 31(10):1729-1737.
Haber et al. *J. Cardiovasc. Pharmacol.* 1988, 10 (Suppl. 7):S54-S58.

*Primary Examiner*—Merrell C. Cashion, Jr.
*Assistant Examiner*—Bennett Celsa
*Attorney, Agent, or Firm*—Elizabeth M. Anderson

[57] ABSTRACT

The invention concerns novel renin-inhibitory compounds which are useful for treating renin-associated hypertension, congestive heart failure, hyperaldosteronism, glaucoma, and diseases caused by retroviruses including HTLV-I -II, and -III. Processes for preparing the compounds, novel intermediates useful in the preparation thereof, compositions containing them, and methods of using them are included. Also included is a diagnostic method which uses the compounds to determine the presence of renin-associated hypertension, congestive heart failure, or hyperaldosteronism.

9 Claims, No Drawings

RENIN INHIBITING PEPTIDES HAVING AN α-HETEROATOM AMINO ACID AT THE P₃ POSITION

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney, and other tissues to an octapeptide, angiotensin II. Angiotensin II raises blood pressure both directly by causing arteriolar constriction and indirectly by simulating release of the sodium-retaining hormone aldosterone from the adrenal gland causing a rise in extracellular fluid volume. Inhibitors of renin have been sought as agents for control of hypertension and hyperaldosteronism.

The present invention concerns novel peptides which inhibit renin. It also concerns pharmaceutical compositions containing these novel peptides, methods of treating renin-associated hypertension, congestive heart failure, glaucoma, and hyperaldosteronism, as well as the use of the peptides as diagnostic tools, and the methods for preparing the peptides.

Since HIV protease, like renin, is an aspartyl protease, these compounds can also be used to treat diseases caused by retroviruses including HTLV-I, -II, and -III.

EPA 229667 discloses certain peptidylaminodiols as renin inhibiting compounds of the formula

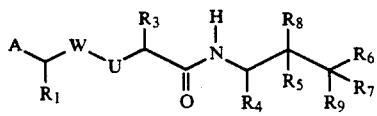

wherein A is a substituent; W is C=O or CHOH, U is $CH_2$ or $NR_2$, provided that when W is CHOH then U is $CH_2$; $R_1$ is loweralkyl, cycloalkylmethyl, benzyl, 4-methoxy-benzyl, halobenzyl, (1-naphthyl)methyl, (2-naphthyl)-methyl, (4-imidazoyl)methyl, α,α-dimethylbenzyl, 1-benzyloxyethyl, phenethyl, phenoxy, thiophenoxy or anilino; $R_2$ is hydrogen or loweralkyl; $R_3$ is loweralkyl, [(alkoxy)alkoxy]alkyl, [thioalkoxyalkyl, loweralkenyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or loweralkyl; $R_8$ and $R_9$ are independently selected from OH and $NH_2$; and $R_6$ is hydrogen, loweralkyl, vinyl or arylalkyl; provided that when $R_5$ and $R_7$ are both hydrogen and $R_8$ and $R_9$ are OH, the carbon bearing $R_5$ is of the "R" configuration and the carbon bearing $R_6$ is of the "S" configuration, or pharmaceutically acceptable salts or esters thereof.

EPA 202577 discloses certain N-(acyldipeptidyl)-aminoglycols of formula

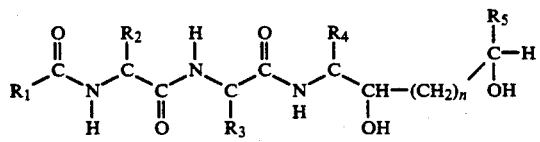

wherein $R_1$ is alkoxy containing one to six carbon atoms or lower alkyl containing one to six carbon atoms; $R_2$ is benzyl or naphthylmethyl, $R_3$ is lower alkyl containing one to six carbon atoms or imidazole-methyl; $R_4$ is benzyl, $R_5$ is hydrogen or lower alkyl, and n is 0 or 1. These compounds are useful as renin inhibitors.

The novel peptides of this invention all have an α-heteroatom amino acid at the $P_3$ position. A designation of the various positions occupied by the amino acids is illustrated by:

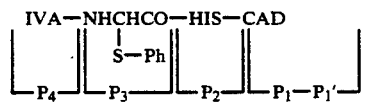

It is surprising to find such blood activity in these compounds.

SUMMARY

The present invention relates to novel peptides of the formula $$A-X-Y-W-U \qquad (I)$$

and the pharmaceutically acceptable acid addition salts thereof wherein A, X, Y, W, and U are as defined herein below.

The invention also includes pharmaceutical compositions comprising an effective amount of the above peptide of formula 1 in admixture with a pharmaceutically acceptable carrier or excipient and a method for treating renin-associated hypertension in a patient suffering therefrom comprising administering to said patient the above pharmaceutical composition in unit dosage form.

Further, the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

Further, the invention includes a pharmaceutical composition comprising an effective amount of a peptide of formula I above in admixture with a pharmaceutically acceptable carrier or excipient and a method for treating congestive heart failure in a patient suffering therefrom comprising administering to said patient the above pharmaceutical composition in unit dosage form.

The invention also includes a pharmaceutical composition comprising an effective amount of a peptide of formula I above in admixture with a pharmaceutically acceptable carrier or excipient, and a method for treating diseases caused by retroviruses HTLV-I, -II, and -III in a patient suffering therefrom comprising administering to said patient the above pharmaceutical composition in unit dosage form.

The invention also includes a pharmaceutical composition comprising an effective amount of a peptide of formula 1 above in admixture with a pharmaceutically acceptable carrier or excipient, and a method for treating glaucoma in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above and novel intermediates useful in the preparation of the peptides.

DETAILED DESCRIPTION

The following table provides a dictionary of the terms used in the description of the invention.

TABLE I

| Abbreviated Designation | |
|---|---|
| | Amino Acid |
| HIS | L-Histidine |
| LEU | L-Leucine |
| TZA | 2(S)-Amino-3-(4-thiazolyl)-propanoic acid |
| ALG | 2(S)-Amino-4-pentenoic acid (allylglycine) |
| PPG | 2(S)-Amino-4-pentynoic acid (propargylglycine) |
| NLE | L-Norleucine |
| STA | 4(S)-Amino-3(S)-hydroxy-6-methyl-heptanoic acid |
| PHSTA | 4(S)-Amino-3(S)-hydroxy-5-phenyl-pentanoic acid |
| CYSTA | 4(S)-Amino-3(S)-hydroxy-5-cyclo-hexanepentanoic acid |
| ASTA | 3(R,S),4(S)-Di-amino-6-methyl-heptanoic acid |
| ACYS | 3(R,S),4(S)-Di-amino-5-cyclo-hexanebutanoic acid |
| CHSTA | 4(S)-Amino-3(S)-hydroxy-4-cyclo-hexanebutanoic acid |
| DFSTA | 4(S)-Amino-3(S)-hydroxy-2,2-difluoro-6-methyl-heptanoic acid |
| DFKSTA | 4(S)-Amino-3-oxo-2,2-difluoro-6-methylheptanoic acid |
| DFCYS | 4(S)-Amino-3(S)-hydroxy-2,2-di-fluoro-5-cyclo-hexanepentanoic acid |
| DFKCYS | 4(S)-Amino-3-oxo-2,2-difluoro-5-cyclohexane-pentanoic acid |
| DFCHS | 4(S)-Amino-3(S)-hydroxy-2,2-di-fluoro-4-cyclo-hexanebutanoic acid |
| DFKCHS | 4(S)-Amino-3-oxo-2,2-difluoro-4-cyclohexane-butanoic acid |
| CDH | 2(S)-Amino-3(S), 5(R,S)-dihydroxy-1-cyclohexylheptane |
| CAF | 2(S)-Amino-3(S), 5(R,S)-dihydroxy-1-cyclohexyl-6-methylheptane |
| CHE | 2(S)-Amino-3(S), 5(R,S)-dihydroxy-1-cyclohexyl-6-heptene |
| CAD | 2(S)-Amino-1-cyclohexyl-3(R), 4(S)-dihydroxy-6-methylheptane |
| | Acyl Group |
| Z | Benzyloxycarbonyl |
| BOC | Tert-butyloxy-carbonyl |
| BMA | 3-Amino-3-methyl-butanoyl |
| Z-BMA | 3-(Benzyloxycar-bonylamino)-3-methylbutanoyl |
| IVA | Isovaleryl |
| NVA | n-Valeryl |
| SMO | Morpholinosulfamyl |
| SME | Dimethylamino-sulfamyl |
| | Amides With |
| —NHCH₂Ph | Benzylamine |
| —NHCH₂-(cyclohexyl) | Cyclohexylmethyl-amine |
| —NHCH₂-(phenyl)-CH₂NHZ (BOC) | m-Xylene-di-amine (Z or BOC) |
| —NHCH₂-(phenyl)-CH₂NH₂ | m-Xylene-di-amine |
| —NH₂ | Ammonia |
| —NH-(piperidinyl)-N—CH₂Ph | 4-Amino-N-benzyl-piperidine |
| —NH-(piperidinyl)-NH | 4-Aminopiperidine |
| —NH—CH₂-(2-pyridyl) | 2-Aminomethyl-pyridine |
| MBA | 2-Methylbutylamine |
| —NH—CH(CH₂OH)—CH(CH₃)CH₂CH₃ | 1-Hydroxymethyl-2-methylbutylamine |
| AEM | 4-(2-Aminoethyl)-morpholine |
| | Protecting Group |
| TRT | Trityl |
| | Esters With |
| —OCH₃ | Methanol |
| —OC₂H₅ | Ethanol |
| O-t-Bu | t-Butanol |
| O-i-Pr | Isopropanol |
| | Solvents and Reagents |
| DMF | N,N-Dimethyl-formamide |
| HOBT | Hydroxybenzo-triazole hydrate |
| DCC | N,N'-Dicyclohexyl-carbodiimide |
| HOAc | Acetic acid |
| Et₃N | Triethylamine |

TABLE I-continued

| Abbreviated Designation | |
|---|---|
| THF | Tetrahydrofuran |
| EtOH | Ethanol |
| MeOH | Methanol |
| Et₂O | Diethylether |
| EtOAc | Ethyl acetate |
| NBS | N-Bromo-succinimide |

The peptides of the instant invention are of formula $$A-X-Y-W-U \qquad \text{I}$$

or a pharmaceutically acceptable salt thereof wherein A is BOC, IVA, NVA, BMA,

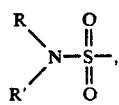

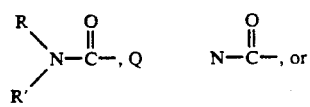

wherein R and R' are each independently hydrogen or a straight or branched lower alkyl,

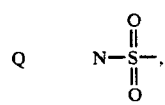

is a saturated ring containing from two to five carbon atoms and Q is CH₂, oxygen, sulfur or NR;

X is 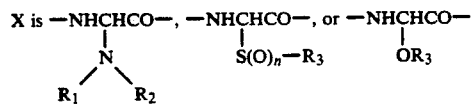

wherein R₁ and R₂ are each independently hydrogen, straight or branched lower alkyl, lower alkenyl, lower alkynyl or aryl and when R₁ and R₂ are alkyl, they may be joined to form a 5- or 6-membered ring. Only one of R₁, R₂ may be H; R₃ is straight or branched lower alkyl, lower alkenyl, lower alkynyl, aryl, or heteroaryl; n is 0, 1, or 2.

Y is HIS, TZA,

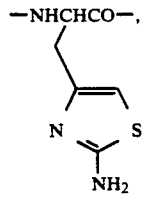

LEU, NLE,

LYS(COH),      LYS(COCH₃), OLYS(NHCSNHCH₃)

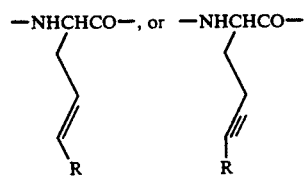

wherein R₄ is straight or branched lower alkyl, alkenyl, or alkynyl;

W is CAD, CAH, STA, CYSTA, PHSTA, ASTA, ACYS, DFSTA, DFKSTA, DFCYS, DFKCYS, DFCHS or DFKCHS, CDH, CAF, or CHE; and U is MBA, AEM, —NHCH₂Ph,

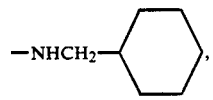

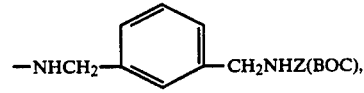

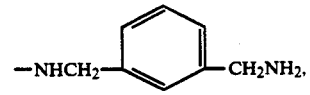

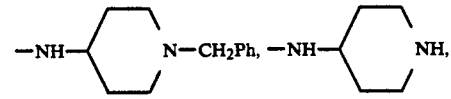

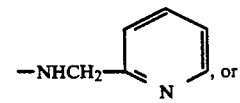

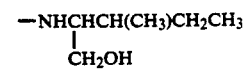

with the proviso that when W is CAD or CAH, U is absent.

Preferred compounds of the instant invention are those of formula I wherein
A is IVA, BOC, BMA, SMO, SME,

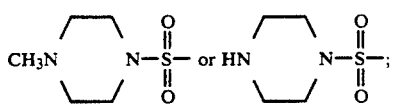

X is —NHCHCO—, —NHCHCO—, or

—NHCHCO— wherein $R_1$
    |
    $OR_3$ and $R_2$ are each independently hydrogen, $CH_3$, $C_2H_5$, or phenyl and $R_3$ is phenyl, $CH_3$, $C_2H_5$, i—$C_3H_7$, —$CH_2CH=CH_2$, or —$CH_2C\equiv CH$ and n is 0;
Y is HIS, TZA,

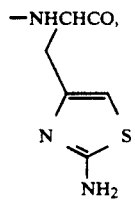

ALG, LEU or

—NHCHCO ;
    |
    $CO_2CH_3$

W is CAD, CYSTA, DFCYS, CDH, CAF, or DFKCYS; and
U is MBA, AEM, —$NHCH_2Ph$,

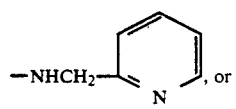

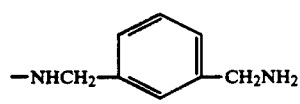

with the proviso that when W is CAD, U is absent.
More preferred compounds of the instant invention are those of formula I wherein
A is IVA or BOC;

X is —NHCHCO—, —NHCHCO—, —NHCHCO—,
       |            |            |
       S—Ph         O—Ph         S—$CH(CH_3)_2$

—NHCHCO—, —NHCHCO—, or
    |            |
    $SO_2CH(CH_3)_2$   NH—Ph

—NHCHCO—;
    |
    N—Ph
    |
    $CH_3$

Y is HIS or LEU;
W is CAD or STA; and
U is MBA.

Still more preferred compounds of the instant invention are selected from the group consisting of:
IVA-NHCH(SPh)CO-HIS-CAD,
IVA-NHCH(SPh)CO-LEU-STA-MBA (Isomer A),
IVA-NHCH(SPh)CO-LEU-STA-MBA (Mixture of diastereomers),
IVA-NHCH(OPh)CO-HIS-CAD,
IVA-NHCH(SCH($CH_3$)$_2$)CO-HIS-CAD (Isomer A),
IVA-NHCH(SCH($CH_3$)$_2$)CO-HIS-CAD (Isomer B),
IVA-NHCH($SO_2CH(CH_3)_2$)CO-HIS-CAD,
BOC-NHCH(SCH($CH_3$)$_2$)CO-LEU-STA-MBA,
IVA-NHCH(NHPh)CO-HIS-CAD,
IVA-NHCH(N($CH_3$)Ph)CO-HIS-CAD, and
IVA-NHCH(NHPh)CO-LEU-STA-MBA.

Other preferred compounds of the invention are:
IVA-NHCH(SPh)CO-HIS-CYSTA-AEM,
IVA-NHCH(SPh)CO-HIS-PHSTA-AEM,
IVA-NHCH(SPh)CO-HIS-DFCYS-AEM,
IVA-NHCH(SPh)CO-HIS-DFKCYS-AEM,
IVA-NHCH(SPh)CO-HIS-ACYS-AEM,
IVA-NHCH(SCH($CH_3$)$_2$)CO-HIS-DFCYS-AEM,
IVA-NHCH(SCH($CH_3$)$_2$)CO-HIS-DFKCYS-AEM,
IVA-NHCH(SCH($CH_3$)$_2$)CO-HIS-CYSTA-AEM,
IVA-NHCH(SCH($CH_3$)$_2$)CO-HIS-ACYS-AEM,
IVA-NHCH($SCH_3$)CO-HIS-CAD,
IVA-NHCH($SC_2H_5$)CO-HIS-CAD,
IVA-NHCH($SC_3H_7$)CO-HIS-CAD,
IVA-NHCH($SCH_2CH=CH$)CO-HIS-CAD,
IVA-NHCH($SCH_2C\equiv CH$)CO-HIS-CAD,
IVA-NHCH($SCH_3$)CO-HIS-CYSTA-AEM,
IVA-NHCH($SCH_3$)CO-HIS-DFKCYS-AEM,
IVA-NHCH($SC_2H_5$)CO-HIS-CYSTA-AEM,
IVA-NHCH($SC_2H_5$)CO-HIS-DFKCYS-AEM,
IVA-NHCH($SC_3H_7$)CO-HIS-DFKCYS-AEM,
IVA-NHCH($SCH_3H_7$)CO-HIS-CYSTA-AEM,
IVA-NHCH($SCH_2CH=CH_2$)CO-HIS-CYSTA-AEM,
IVA-NHCH($SCH_2CH=CH_2$)CO-HIS-DFKCYS-AEM,
IVA-NHCH($SCH_2C\equiv CH$)CO-HIS-CYSTA-AEM,
IVA-NHCH($SCH_2C\equiv CH$)CO-HIS-DFKCYS-AEM,
IVA-NHCH(N($CH_3$)Ph)CO-HIS-CYSTA-AEM,
IVA-NHCH(N($CH_3$)Ph)CO-HIS-DFKCYS-AEM,
IVA-NHCH(NHPh)CO-HIS-CYSTA-AEM,
IVA-NHCH(NHPh)CO-HIS-DFKCYS-AEM,
SMO-NHCH(SPh)CO-HIS-CAD,
SMO-NHCH(SPh)CO-HIS-CYSTA-AEM,
SMO-NHCH(SPh)CO-HIS-DFKCYS-AEM,
SMO-NHCH(SCH($CH_3$)$_2$)CO-HIS-CAD,
SMO-NHCH(SCH($CH_3$)$_2$)CO-HIS-CYSTA-AEM,
SMO-NHCH(SCH($CH_3$)$_2$)CO-HIS-DFKCYS-AEM,
SMO-NHCH($SCH_3$)CO-HIS-CAD,
SMO-NHCH($SC_2H_5$)CO-HIS-CAD,
SMO-NHCH($SC_3H_7$)CO-HIS-CAD,
SMO-NHCH($SCH_2CH=CH_2$)CO-HIS-CAD,
SMO-NHCH($SCH_2C\equiv CH$)CO-HIS-CAD,
SMO-NHCH(N($CH_3$)Ph)CO-HIS-CAD,
SMO-NHCH(NHPh)CO-HIS-CAD,
SMO-NHCH(OPh)CO-HIS-CAD,

9

SMO-NHCH(SPh)CO-TZA-CAD,
SMO-NHCH(SCH₂CH=CH₂)CO-TZA-CAD,
SMO-NHCH(SCH₂C≡CH)CO-TZA-CAD,

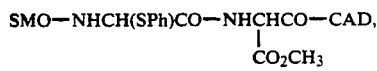

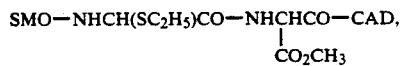

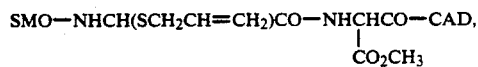

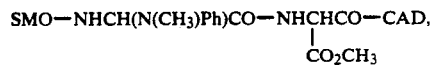

SMO-NHCH(SPh)CO-ALG-CAD,

10

SMO-NHCH(SCH(CH₃)₂)CO-ALG-CAD,
SMO-NHCH(SCH₂CH=CH₂)CO-ALG-CAD,
SMO-NHCH(OPh)CO-ALG-CAD,
SMO-NHCH(N(CH₃)Ph)CO-ALG-CAD,
SMO-NHCH(SPh)CO-LEU-CAD,
SMO-NHCH(SC₂H₅)CO-LEU-CAD,
SMO-NHCH(N(CH₂)Ph)CO-LEU-CAD,
SMO-NHCH(SPh)CO-LYS(COCH₃)-CAD,
SMO-NHCH(SC₃H₇)CO-LYS(COCH₃)-CAD,
SMO-NHCH(SCH₂CH=CH₂)CO-LYS(COCH₃)-CAD,
SMO-NHCH(N(CH₃)Ph)CO-LYS(COCH₃)-CAD,
SMO-NHCH(NHPh)CO-LYS(COCH₃)-CAD,
SMO-NHCH(OPh)CO-TZA-CAD,
SMO-NHCH(N(CH₂)Ph)CO-TZA-CAD,
SMO-NHCH(SCH₃)CO-TZA-CAH,
SMO-NHCH(SCH₃)CO-HIS-CAH,
SMO-NHCH(SC₃H₇)CO-LYS(NHCSNHCH₃)-CAD,

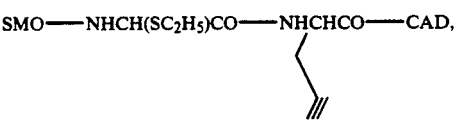

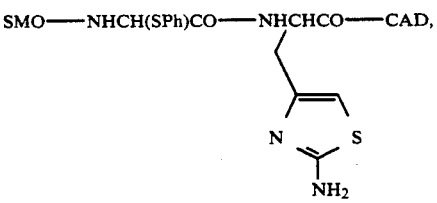

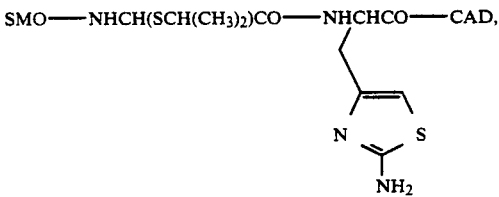

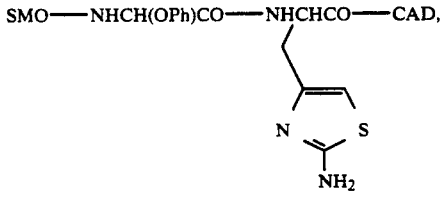

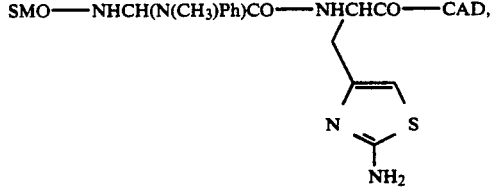

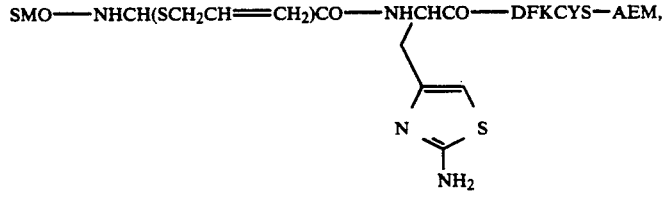

SME-NHCH(SPh)CO-HIS-CAD,

SME-NHCH(N(CH₃)Ph)CO-HIS-CAD,
SME-NHCH(SCH(CH₃)₂)CO-HIS-CAD,

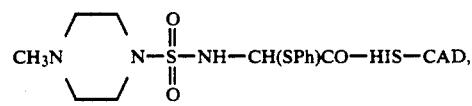

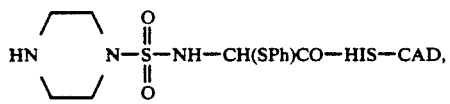

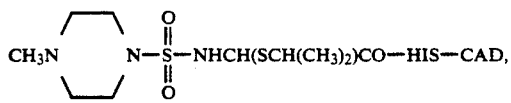

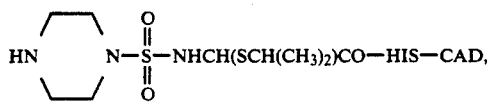

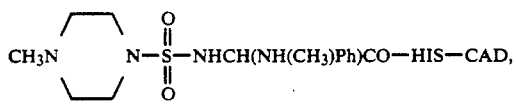

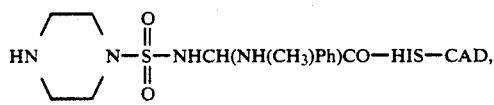

SMO-NH(SPh)CO-HIS-CDH,
SMO-NHCH(SCH(CH₃)₂)CO-HIS-CAF,
SMO-NHCH(OPh)CO-HIS-CHE,

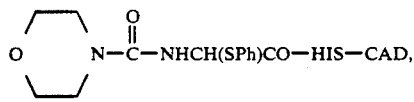

and

The term lower alkyl refers to straight or branched chain hydrocarbon radicals containing from one to ten carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethyl-propyl, n-hexyl and the like or as otherwise specified.

Lower alkenyl means a straight or branched chain hydrocarbon radical of from one to ten carbon atoms containing a double bond. This includes but is not limited to allyl and methylallyl.

Lower alkynyl means a straight or branched chain hydrocarbon radical of from one to ten carbon atoms containing a triple bond. This includes but is not limited to propargyl.

Aryl means phenyl, naphthyl or other aromatic groups, including mono- or bicyclic, which may be substituted, especially monosubstituted, by F, Cl, Br, I, CF₃, OH, OR, or R, wherein R is lower alkyl.

Heteroaryl means a heterocyclic aromatic 6-membered ring compound containing one to three nitrogen atoms or a 5-membered ring compound containing a single heteroatom selected from nitrogen, oxygen, and sulfur or more than one heteroatom provided that the additional heteroatom(s) is/are nitrogen. The heteroaryl aryl group may be unsubstituted or monosubstituted with halogen, lower alkyl, amino, alkylamino, dialkylamino, or hydroxyl. Preferred heteroaryls are thiophene, furan, pyrrole, imidazole, or thiazole.

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) and S(L) configuration. The present invention includes all enantiomeric and epimeric forms as well as the appropriate mixtures thereof.

Novel intermediates of the present invention include he following compounds:
IVA-NHCH(SPh)CO₂H,
IVA-NHCH(OPh)CO₂H,
IVA-NHCH(SCH(CH₃)₂CO₂H, and
BOC-NHCH(SCH(CH₃)₂)CO₂H.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following schemes illustrate novel methods of preparing certain peptides of the present invention.

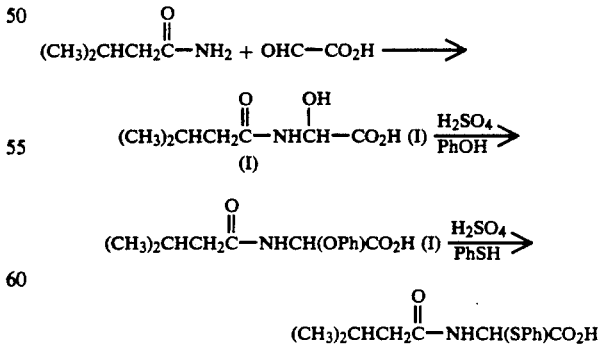

-continued
SCHEME II

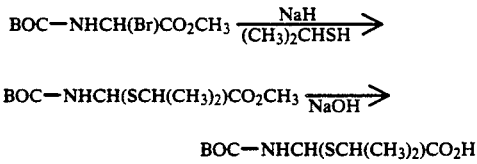

SCHEME III

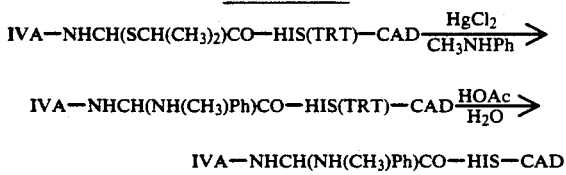

SCHEME IV

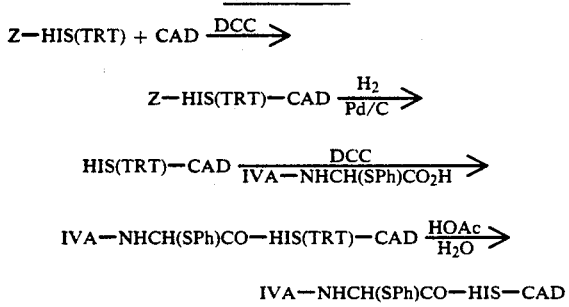

The intermediates of Scheme I are novel an are prepared by an adaptation of a method described by U. Zollner and D. Ben-Ishai, Tetrahedron 31, 863 (1975). Those compounds bearing an α-oxygen atom are prepared in the following manner. IVA-NH$_2$ and glyoxylic acid hydrate are heated in Et$_2$O for 4 to 48 hours, giving the α-OH compound I. I is dissolved in dioxane and cooled to 0°. Phenol s added and the indioxane and cooled to 0°. Phenol is added and the mixture treated with concentrated H$_2$SO$_4$. The mixture is allowed to warm to room temperature for 8 to 72 hours giving the α-phenoxy compound The α-sulfur atom derivatives may also be prepared from the α-hydroxy compound I. In this procedure I is dissolved in HOAc, cooled to 0°, and treated with concentrated H$_2$SO$_4$ and the appropriate mercaptan. After stirring at room temperature for one to four days, the α-mercapto derivative can be isolated.

The α-sulfur derivatives may also be prepared according to Scheme II. BOC-GLY-OCH$_3$ can be brominated with NBS according to P. Emmert, et al, Tet.

Letters, 29, 1265 (1988). Treatment with the anion of an alkyl mercaptan gives the α-sulfur derivative. Basic hydrolysis of the ester gives the desired intermediate.

The novel α-amino derivatives can be prepared according to Scheme III from the completed peptide. The peptide is dissolved in THF, cooled to −60° and treated with mercuric chloride. The appropriate amine is then added and the mixture is allowed to warm to room temperature over 4 to 24 hours, giving the desired product. This procedure is an adaptation of that described by M. G. Bock, R. M. DiPardo, and R. Freidinger, J. Org. Chem. 51, 3718 (1986). The TRT protecting group can be removed by warming for 5 to 10 minutes at 80°-90° in 80% aqueous HOAc.

The peptides of the invention are prepared as outlined in Scheme IV. Z-HIS(TRT) is coupled with CAD in the presence of DCC and HOBT. The Z-protecting group is then removed with H$_2$ in the presence of Pd/C and then is in turn coupled with IVA-NHCH(SPh)CO$_2$H in the presence of DCC and HOBT. The trityl protecting group is removed with HOAc/HO in a final step to give the peptides of the instant invention.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the percent inhibition at the specified molar concentration or as the IC$_{50}$, which is the molar concentration of test compound causing a 50% inhibition of the renin activity.

TABLE II

| Compound | In Vitro Activity |
| --- | --- |
| IVA-NHCH(SPh)CO—HIS—CAD | $1.5 \times 10^{-9}$* |
| IVA-NHCH(SPh)CO—LEU—STA—MBA (Isomer A) | $1.4 \times 10^{-7}$* |
| IVA-NHCH(SPh)CO—LEU—STA—MBA (Mixture of diastereomers) | $1.9 \times 10^{-7}$* |
| IVA-NHCH(OPh)CO—HIS—CAD | $3.0 \times 10^{-6}$* |
| IVA-NHCH(SCH(CH$_3$)$_2$)CO—HIS—CAD (Isomer A) | 10.5% @ $10^{-8}$ |
| IVA-NHCH(SCH(CH$_3$)$_2$)CO—HIS—CAD (Isomer B) | $5.7 \times 10^{-9}$* |
| IVA-NHCH(SO$_2$CH(CH$_3$)$_2$)CO—HIS—CAD | 8.2% @ $10^{-8}$ |
| BOC—NHCH(SCH(CH$_3$)$_2$)CO—LEU—STA—MBA | 23% @ $10^{-6}$ |
| IVA-NHCH(NHPh)CO—HIS—CAD | $1.3 \times 10^{-8}$* |
| IVA-NHCH(N(CH$_3$)Ph)CO—HIS—CAD | $3.5 \times 10^{-9}$* |
| IVA-NHCH(NHPh)CO—LEU—STA—MBA | 24% @ $10^{-6}$ |

*IC$_{50}$

As can be seen from the above table, the compounds of the present invention have a significant effect on the activity of renin and thus are useful for the treatment of hypertension, congestive heart failure, and hyperaldosteronism.

Many of the compounds of this invention show the desirable property of being selective for the renin enzyme when compared to pepsin and cathepsin D.

For preparing pharmaceutical compositions from the compounds described by this invention, inert, pharmaceutically acceptable carriers can be either solid or liquid. Solid form preparations include powders, tablets, dispersible granules, capsules, Cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methyl-cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, inramuscular, inrasternal injection or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify. Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit Alternately, sufficient solid may be provided so hat after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid-doses at low temperature (.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard o he route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70-kg subject is from 1 to 1500 mg per day or preferably 25 to 750 mg per day optionally divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

A solution of 2.2 g (2.52 mmole) of IVA-NHCH(SPh)-CO-HIS(TRT)-CAD in 25 ml of 80% HOAc was heated on a steam bath for five minutes, then left standing at room temperature for one hour. The mixture was filtered and the filtrate evaporated under reduced pressure. The residue was triturated with $H_2O$ and $Et_2O$ giving 1.12 g of the product as a mixture of diastereomers as a yellow solid. The structure was confirmed by NMR and mass spectroscopy.

Calcd. for $C_{33}H_{51}N_5O_5S$ (MW 629.87):
C, 62.93; H, 8.16; N, 11.11
Found: C, 62.59; H, 8.27; N, 10.93

EXAMPLES 2 AND 3

IVA-NHCH(SPh)-CO-LEU-STA-MBA

A solution of 2.7 g (10.1 mmole) of IVA-NHCH-(SPh)-$CO_2H$, 3.6 g (10.1 mmole) of LEU-STA-MBA, and 1.4 g (10.4 mmole) of HOBT in 150 ml DMF was cooled in ice and treated with 2.15 g (10.4 mmole) of DCC. After stirring at room temperature overnight, he mixture was filtered and he solvent removed under high vacuum. The residue was taken up in $EtOAc/CH_2Cl_2$ (1/1) and washed with 1N citric acid, saturated NaCl, saturated $NaHCO_3$, and saturated NaCl. Drying over $MgSO_4$ and removal of the solvent under reduced pressure gave the crude product. Chromatography on silica gel, eluting with $EtOAc/CHCl_3$ (1/1) gave an oil. Thin layer showed the diastereomers present as two distinct spots. The oil was taken up in a minimal amount of $CHCl_3$ and precipitated by the addition of $Et_2O$. There was obtained 2.02 g of product. Thin layer showed this to be the faster moving diastereomer. The structure was confirmed by NMR and mass spectroscopy.

Calcd. for $C_{32}H_{54}N_4O_5S$ (MW 606.87):
C, 63.33; H, 8.97; N, 9.19
Found: C, 63.75; H, 9.30; N, 9.54

The filtrate from above was concentrated and the residue rechromatographed on silica gel, eluting with EtOAc/CHCl$_3$ (1/1). There was obtained 3.48 g of product as a mixture of diastereomers. The structure was confirmed by NMR and mass spectroscopy.

Calcd. for $C_{32}H_{54}N_4O_5S$ (MW 606.87):
C, 63.33; H, 8.97; N, 9.19
Found: C, 63.35; H, 9.15; N, 9.19

EXAMPLE 4

IVA-NHCH-(OPh)CO-HIS-CAD

A solution of 1.82 g (2.13 mmole) of IVA-NHCH-(OPh)CO-HIS(TRT)-CAD in 25 ml of 80% HOAc was heated on a steam bah for five minutes, then left standing at room temperature for four hours. The mixture was filtered and he filtrate diluted with H$_2$O. The pH was adjusted to 8.0 with solid NaHCO$_3$, and the solution extracted with EtOAc. The organic phase was washed with brine, diluted with MeOH/CHCl$_3$ (1/1) and dried over MgSO$_4$. The solution was reduced in volume and added to Et$_2$O to give 0.52 g of the product as a solid. The structure was confirmed by NMR and mass spectroscopy.

Calcd. for $C_{33}H_{51}N_5O_6 \cdot 0.5H_2O$ (MW 622.81):
C, 63.64; H, 8.41; N, 11.24
Found: C, 63.81; H, 8.44; N, 11.12

EXAMPLE 5

IVA-NHCH(SCH(CH$_3$)$_2$)CO-HIS-CAD (Isomer A)

A solution of 2.0 g (2.39 mmole) of IVA-NHCH-(SCH(CH$_3$)$_2$)CO-HIS(TRT)-CAD (faster eluting isomer) in 50 ml 80% HOAc was heated on a steam bath for seven minutes, then allowed to stand at room temperature for one hour. The mixture was filtered and the filtrate evaporated to a syrup. The syrup was mixed with H$_2$O, giving a white solid. Chromatography on silica gel, eluting with CHCl$_3$/MeOH (9/1) gave 0.98 g of the product as a white solid. The structure was confirmed by NMR and mass spectroscopy Calcd. for $C_{30}H_{53}N_5O_5S$ (MW 595.88):
C, 60.47; H, 8.96; N, 11.75
Found: C, 60.61; H, 9.11; N, 11.71

EXAMPLE 6

IVA-NHCH-(SCH(CH$_3$)$_2$)CO-HIS-CAD (Isomer B)

A solution of 2.0 g (2.39 mmole) of IVA-NHCH-(SCH(CH$_3$)$_2$)CO-HIS(TRT)-CAD (slower eluting isomer) in 50 ml of 80% HOAc was heated on a steam bath for seven minutes, diluted with 20 ml H$_2$O, and allowed to stand at room temperature for one hour. The mixture was filtered and the filtrate evaporated to a syrup. Adding the syrup to H$_2$O gave a gelatinous solid which was collected and taken up in THF. Adding this to Et$_2$O gave a solid. The solid was taken up in MeOH/THF and diluted with Et$_2$O to give 0.91 g of the product as a white solid. The structure was confirmed by NMR and mass spectroscopy.

Calcd. for $C_{30}H_{53}N_5O_5S \cdot 0.6HOAc$ (MW 647.88):
C, 57.84; H, 8.62; N, 10.81
Found: C, 57.64; H, 8.92; N, 10.89

EXAMPLE 7

IVA-NHCH(SO$_2$CH(CH$_3$)$_2$)CO-HIS-CAD

A solution of 0.9 g (1.03 mmole) of IVA-NHCH-(SO$_2$CH(CH$_3$)$_2$)CO-HIS(TRT)-CAD in 20 ml 80% HOAc was heated on a steam bath for six minutes, then allowed to stand at room temperature for two hours. The mixture was filtered and the filtrate evaporated to a paste. Trituration with Et$_2$O gave a solid which was collected and washed with Et$_2$O and H$_2$O to give 0.41 g of the product as a white solid. The structure was confirmed by NMR and mass spectroscopy Calcd. for $C_{30}H_{53}N_5O_7S$ (MW 627.85):
C, 57.39; H, 8.51; N, 11.15
Found: C, 57.48; H, 8.72; N, 11.15

EXAMPLE 8

BOC-NHCH(SCH-(CH$_3$)$_2$)CO-LEU-STA-MBA

A solution of 2.99 g (12 mmole) of BOC-NHCH(SCH-(CH$_3$)$_2$CO$_2$H, 4.3 g (12 mmole) of LEU-STA-MBA, and 1.7 g (12.6 mmole) of HOBT in 150 ml CH$_2$Cl$_2$ was cooled in ice and treated with 2.6 g (12.6 mmole) of DCC. After stirring at room temperature overnight, the mixture was filtered and the solvent removed. The residue was taken up in CHCl$_3$ and washed with 1N citric acid, saturated NaCl, saturated NaHCO$_3$, and saturated NaCl. Drying over MgSO$_4$ and removal of the solvent under reduced pressure ave the crude product. Chromatography on silica gel, eluting with a gradient of 0–5% MeOH in CHCl$_3$ gave 3.95 g of the product as a white solid. The structure was confirmed by NMR and mass spectroscopy Calcd. for $C_{29}H_{56}N_4O_6S$ (MW 588.85):
C, 59.15; H, 9.85; N. 9.51
Found: C, 59.16; H, 10.09; N, 9.59

EXAMPLE 9

A solution of 2.32 (2.71 mmole) of IVA-NHCH-(NHPh)CO-HIS(TRT)-CAD in 50 ml HOAc was heated on a steam bath for five minutes, 20 ml H$_2$O added, and the mixture left at room temperature for two hours. The mixture was filtered and filtrate evaporated to an oil under reduced pressure. The oil was taken up in EtOAc and washed with saturated NaCl, saturated NaHCO$_3$, and saturated NaCl. After drying over MgSO$_4$, the EtOAc was diluted with Et$_2$O, giving the crude product as a solid. Chromatography on silica gel, eluting with CHCl$_3$/MeOH (95/5) gave 0.75 g of the product as a white solid. The structure was confirmed by NMR and mass spectroscopy Calcd. for $C_{33}H_{52}N_6O_5 \cdot 0.25CHCl_3 \cdot 0.4H_2O$ (MW 619.81):
C, 63.99; H, 8.59; N, 13.56
Found: C, 63.73; H, 8.58; N, 13.20

EXAMPLE 10

IVA-NHCH(N(CH$_3$)Ph)CO-HIS-CAD

Treatment of 2.46 g (2.83 mmole) of IVA-NHCH(N-(CH$_3$)Ph)CO-HIS(TRT)-CAD in a manner similar to that described for Example 9 gave 0.38 g of the product as a white solid. The structure was confirmed by NMR and mass spectroscopy.

Calcd. for $C_{34}H_{54}N_6O_5 \cdot 0.1CHCl_3 \cdot 0.5H_2O$ (MW 648.80):
C, 63 13; H, 8.71; N, 12.95
Found: C, 63.29; H, 8.74; N, 12.84

EXAMPLE 11

IVA-NHCH(NHPh)CO-LEU-STA-MBA

A solution of 2.25 g (3.93 mmole) of IVA-NHCH(SCH-$(CH_3)_2$)CO-LEU-STA-MBA and 1.1 g (11.8 mmole) of aniline in 100 ml THF was treated with 1.6 g (5.9 mmole) of $HgCl_2$ and stirred overnight at room temperature. The mixture was filtered and the filtrate evaporated. The residue was taken up in 125 ml warm EtOAc, filtered, and the filtrate washed with 1N HCl, saturated NaCl, 1N NaOH, and saturated NaCl. Drying over $MgSO_4$ and removal of the solvent left the crude product. Chromatography on silica gel, eluting with EtOAc/$CHCl_3$ (1/1) gave 1.11 g of the product as a white solid. The structure was confirmed NMR and mass spectroscopy.

Calcd. for $C_{32}H_{55}N_5O_5 \cdot 0.25H_2O$ (MW 594.33):
C, 64.67; H, 9.41; N, 11.78
Found C, 64.78; H, 9.37; N, 11.76

INTERMEDIATE FOR EXAMPLE 1

IVA-NHCH-(SPh)CO-HIS(TRT)-CAD

A solution of 0.785 g (2.94 mmole) of IVA-NHCH-(SPh)$CO_2H$ and 0.4 g (2.98 mmole) of HOBT in 100 ml $CH_2Cl_2$ and 10 ml DMF was cooled in ice and treated with 1.83 g (2.94 mmole) of HIS(TRT)-CAD followed by 0.62 g (2.98 mmole) of DCC. After stirring at room temperature overnight, the mixture was filtered and the solvent removed under reduced pressure The residue was taken up in EtOAc, filtered, and washed with 1N citric acid, saturated NaCl, saturated $NaHCO_3$, and saturated NaCl. Drying over $MgSO_4$ and removal of he solvent ave the crude product. Chromatography on silica gel, eluting with EtOAc/$CHCl_3$ (1/1) gave 2.25 g of the product as a mixture of diastereomers as a yellow foam. The structure was confirmed by NMR and mass spectroscopy.

INTERMEDIATE FOR EXAMPLES 1-3

IVA-NHCH(SPh)$CO_2H$

A solution of 20.0 (0.114 mole) of IVA-NHCH-(OH)-$CO_2H$ in 90 ml HOAc was treated with 25.0 g (0.228 mole) of thiophenol and 10 ml of concentrated $H_2SO_4$ and stirred at room temperature for 72 hours. The volume of the mixture was reduced to one-half by evaporation under high vacuum. The residue was diluted with $H_2O$ and extracted with EtOAc. The EtOAc was washed with saturated $NaHCO_3$, the $NaHCO_3$ phase acidified to pH 3 with concentrated HCl, and this extracted with EtOAc. The EtOAc was washed with saturated NaCl and dried over $MgSO_4$. Removal of the solvent under reduced pressure gave 29.58 g of the crude product as a solid. Recrystallization from EtOAc/hexane/$Et_2O$ gave 19.55 g of the product as a white solid. The structure was confirmed by NMR and mass spectroscopy.

INTERMEDIATES FOR EXAMPLE 4

IVA-NHCH-(OPh)$CO_2H$

A solution of 20.0 g (0.114 mole) of IVA-NHCH-(OH)$CO_2H$ n 150 ml dioxane was treated with 26.0 g (0.276 mole) of phenol and 15 ml of concentrated $H_2SO_4$. After stirring for 72 hours at room temperature, the mixture was evaporated and the residue suspended in EtOAc. The suspension was washed with $H_2O$, then twice with saturated $NaHCO_3$. The combined $NaHCO_3$ washes were brought to pH 1 with concentrated HCl and extracted with EtOAc. The EtOAc was washed with saturated NaCl, dried over $MgSO_4$, and the solvent removed, leaving 30.97 g of a syrup. This was taken up in $Et_2O$ and washed with saturated $NaHCO_3$. The $NaHCO_3$ was acidified to pH 1 with concentrated HCl and extracted with $Et_2O$. The $Et_2O$ was washed with saturated NaCl, dried over $MgSO_4$, and the solvent removed, leaving 21.47 g of he product as a white foam. The structure was confirmed by NMR and mass spectroscopy.

IVA-NHCH(OPh)CO-HIS(TRT)-CAD

A solution of 0.74 g (2.79 mmole) of IVA-NHCH-(OPh)$CO_2H$, and 0.38 g (2.85 mmole) of HOBT in 50 ml $CH_2Cl_2$ and 10 ml DMF was cooled in ice and 1.74 g (2.79 mmole) of HIS(TRT)-CAD added, followed by 0.59 g (2.85 mmole) of DCC. After stirring at room temperature overnight, the mixture was filtered, and the filtrate concentrated to an oil under reduced pressure. The oil was taken up in EtOAc and washed with 1N citric acid, saturated NaCl, saturated $NaHCO_3$, and saturated NaCl. Drying over $MgSO_4$ and removal of the solvent under reduced pressure gave 2.53 g of the crude product as an oil. Chromatography on silica gel, eluting with EtOAc/$CHCl_3$ (1/1) gave 1.87 g of the product as a mixture of diastereomers. The material was used in the next step without further purification.

INTERMEDIATES FOR EXAMPLES 5 AND 6

IVA-NHCH-(SCH$(CH_3)_2$)$CO_2H$

A solution of 18.1 g (0.103 mole) of IVA-NHCH-(OH)$CO_2H$ in 90 ml HOAc was treated with 10 ml of concentrated $H_2SO_4$ followed by 15 ml (0.207 mole) of isopropyl mercaptan. After stirring at room temperature for 96 hours, the mixture was concentrated under reduced pressure. The residue was partitioned between 500 ml of EtOAc/$H_2O$ and the phases separated. The EtOAc was washed twice with $H_2O$ and twice with saturated $NaHCO_3$. The $NaHCO_3$ washes were brought to pH 3 with concentrated HCl and extracted with $Et_2O$. The $Et_2O$ was washed with saturated NaCl, dried over $MgSO_4$, and the solvent removed, giving a solid. Recrystallization from $Et_2O$/hexane gave 17.94 g of the product as a white solid. The structure was confirmed by NMR and mass spectroscopy.

IVA-NHCH(SCH-$(CH_3)_2$)CO-HIS(TRT)-CAD

A solution of 4.91 g (21 mmole) of IVA-NHCH(SCH$(CH_3)_2$)$CO_2H$ and 2.85 g (21.5 mmole) of HOBT in 250 ml $CH_2Cl_2$ and 15 ml DMF was cooled in ice and treated with 4.43 g (21.5 mmole) of DCC followed by a solution of 13.97 g (21.0 mmole) of HIS(TRT)-CAD in 100 ml $CH_2Cl_2$. After stirring at room temperature overnight, the mixture was filtered and the filtrate evaporated to an oil. This was taken up in $Et_2O$, filtered, and the filtrate washed with 1N citric acid, saturated NaCl, saturated $NaHCO_3$, and saturated NaCl. Drying over $MgSO_4$ and removal of the solvent gave 18.9 g of the crude product. Chromatography on silica gel, eluting with EtOAc/$CHCl_3$/MeOH (49/49/2) separated the diastereomers present to give 5.89 g of the faster eluting diastereomer and 3.48 g of the slower eluting diastereomer as solids. The structures were confirmed by NMR and mass spectroscopy. There was also obtained 5.71 g of product as a mixture of diastereomers.

INTERMEDIATE FOR EXAMPLE 7

IVA-NHCH(SO$_2$CH(CH$_3$)$_2$)CO-HIS(TRT)-CAD

A solution of 1.0 (1.19 mmole) of IVA-NHCH(SCH-(CH$_3$)$_2$)CO-HIS(TRT)-CAD (fast eluting diastereomer) in 30 ml CH$_2$Cl$_2$ was treated with 0.5 g (2.32 mmole) of m-chloroperbenzoic acid and stirred at room temperature for 30 minutes. The solvent was removed and the residue taken u in EtOAc and washed with saturated NaHCO$_3$, then saturated NaCl. Drying over MgSO$_4$ and removal of the solvent ave 0.97 g of the crude product. Chromatography on silica gel, eluting with a gradient of EtOAc/CHCl$_3$ (1/1) to EtOAc/CHCl$_3$/MeOH (47.5/47.5/5) gave 0.9 g of the product as a mixture of diastereomers, indicating that racemization had occurred at the carbon α to the sulfone. The structure was confirmed by NMR and mass spectroscopy.

INTERMEDIATES FOR EXAMPLE 8

BOC-NHCH(Br)CO$_2$CH$_3$

A solution of 21.76 g (115 mmole) of BOC-GLY-OCH$_3$ in 350 ml CCl$_4$ was treated with 21.5 g (115 mmole) of N-bromosuccinimide and irradiated with a 250-watt sun lamp for one hour at 25°–30°. The residue was taken up in Et$_2$O, dried over MgSO$_4$, and the solvent removed under reduced pressure, giving 30 g of the crude product as an oil. The material was used in the next step without further purification.

BOC-NHCH(SCH(CH$_3$)$_2$)CO$_2$CH$_3$

A suspension of 1.79 g (37.2 mmole) of NaH·oil (50%) in THF was decanted to remove the oil, then resuspended in 150 ml THF. The mixture was treated with 6.89 ml (74.4 mmole) of isopropyl mercaptan and warmed at 40° for two hours to give a white suspension. This was then treated with 11.0 g (37.2 mmole) of BOC-NHCH(Br)CO$_2$CH$_3$ and the mixture stirred at room temperature overnight. The solvent was removed under reduced pressure and the residue taken up in EtOAc and washed with 1N citric acid, saturated NaCl, saturated NaHCO$_2$, and saturated NaCl. Drying over MgSO$_4$ and removal of the solvent gave an oil. Chromatography on silica gel, eluting with hexane/EtOAc (9/1) gave 6.6 g of the product as an oil. The structure was confirmed by NMR and mass spectroscopy.

BOC-NHCH(SCH(CH$_3$)$_2$)CO$_2$H

A solution of 5.28 g (20 mmole) of BOC-NHCH(SCH-(CH$_3$)$_2$)CO$_2$CH$_3$ in 20 ml dioxane was treated with 20 ml of 1N NaOH and stirred at room temperature for one hour, then treated with 15 ml of 1N HCl. The solvent was removed under reduced pressure and the residue suspended in EtOAc. The EtOAc was treated with 6 ml of 1N HCl, separated, and the EtOAc washed with brine. Drying over MgSO$_4$ and removal of the solvent under reduced pressure gave 5.56 g of the product as an oil. The structure was confirmed by NMR and mass spectroscopy.

INTERMEDIATE FOR EXAMPLE 9

IVA-NHCH(NHPh)CO-HIS(TRT)-CAD

A solution of 2.75 g (3.28 mmole) of IVA-NHCH(SCH-(CH$_3$)$_2$)CO-HIS(TRT)-CAD and 0.59 ml (6.44 mmole) of aniline in 100 ml THF was treated with 1.31 g (4.83 mmole) of HgCl$_2$ and stirred at room temperature overnight. The mixture was filtered and the filtrate evaporated to an oil. The oil was taken up in EtOAc and washed with 1N citric acid, saturated NaCl, saturated NaHCO$_2$, and saturated NaCl. Drying over MgSO$_4$ and removal of the solvent gave the crude product. Chromatography on silica gel, eluting with EtOAc/CHCl$_3$ (1/1) gave 2.36 of the product as a solid. The structure was confirmed by NMR and mass spectroscopy.

INTERMEDIATE FOR EXAMPLE 10

IVA-NHCH(N(CH$_3$)Ph)CO-HIS(TRT)-CAD

Treatment of 2.7 (3.22 mmole) of IVA-NHCH(SCH-(CH$_3$)$_2$)CO-HIS(TRT)-CAD with 0.68 ml (6.32 mmole) of N-methylaniline in a manner similar to that described for the intermediate for Example gave 2.61 of the product. The structure was confirmed by NMR and mass spectroscopy.

INTERMEDIATE FOR EXAMPLE 11

IVA-NHCH(SCH(CH$_3$)$_2$)CO-LEU-STA-MBA

A solution of 2.88 g (12.36 mmole) of IVA-NHCH-(SCH(CH$_3$)$_2$)CO$_2$H, 4.42 g (12.36 mmole) of LEU-STA-MBA, and 1.72 g (12.7 mmole) of HOBT in 150 ml CH$_2$Cl$_2$ was cooled to 0° and treated with 2.63 g (12.7 mmole) DCC. After stirring at room temperature for two days, the suspension was filtered and the filtrate evaporated. The residue was taken up in EtOAc/CH$_3$Cl$_2$ (1/1) and washed with 1N citric acid, saturated NaCl, saturated NaHCO$_3$, and saturated NaCl. Drying over MgSO$_4$ and removal of the solvent gave he crude product. Chromatography on silica gel, eluting with CHCl$_3$/EtOAc (1/1) gave 5.78 g of the product as a solid. The structure was confirmed by NMR and mass spectroscopy.

COMMON INTERMEDIATES

ISOVALERYL AMIDE

Isovaleryl chloride (123 g, 1.02 mole) was added dropwise over 45 minutes at −60° to 650 ml THF which had been saturated with NH$_3$ gas. After stirring at room temperature overnight, he solvent was removed under reduced pressure and the residue taken up in EtOAc, and washed with saturated NaHCO$_3$ and saturated NaCl. Drying over MgSO$_4$ and removal of the solvent under reduced pressure ave 62.33 g of the product as a white solid. The structure was confirmed by NMR spectroscopy.

IVA-NHCH(OH)CO$_2$H

A solution of 37.0 g (0.366 mole) of isovaleryl amide and 37.0 g (0.4 mole) of glyoxylic acid hydrate in 500 ml Et$_2$O was heated at reflux for 48 hours. Removal of the solvent under reduced pressure gave 72.0 g of the product as a waxy solid. The material was used in subsequent reactions without further purification.

Z-HIS(TRT)-CAD

A solution of 5.31 g (10.0 mmole) of Z-HIS(TRT) (U.S. Pat. No. 4,735,933) and 2.1 g (10.2 mmole) of HOBT in 100 ml CH$_2$Cl$_2$ and 15 ml DMF was cooled in ice and treated with 2.1 g (10.2 mmole) of DCC. This was then treated with a cold solution of 2.79 g (10.0 mmole) of CAD·HCl (EP-229,667) and 1.42 ml (10.2 mmole) of Et$_3$N in 45 ml of CH$_2$Cl$_2$. After stirring at room temperature overnight, the solvent was removed under reduced pressure and the residue taken up in EtOAc. After filtering off the dicyclohexylurea the filtrate was washed with 1N citric acid, saturated NaCl, saturated NaHCO3, and saturated NaCl. Drying over MgSO4 and removal of he solvent under reduced pressure gave 7.67 g of the crude product as a foam. Chromatography on silica gel, eluting with EtOAc/CHCl3 (1/1) gave 5.69 g of the product as a white solid. The structure was confirmed by NMR and mass spectroscopy.

HIS(TRT)-CAD

A solution of 4.49 g (5.93 mmole) of Z-HIS(TRT)-CAD in 100 ml MeOH was treated with 0.4 g of 20% Pd/C and purged with H2 gas for five hours. The catalyst was filtered off and the solvent removed under reduced pressure. The residue was taken up in Et2O and the solvent removed under reduced pressure giving 3.66 g of the product as a white foam. The structure was confirmed by mass spectroscopy.

BOC-STA-MBA

BOC-STA (27.53 g, 0.1 mole, U.S. Pat. No. 4,397,786) and HOBT (14.2 g, 0.105 mole) were dissolved in 40 ml DMF. 300 ml CH2Cl2 was added, and the mixture was cooled to 0°. A solution of DCC (21.66 g, 0.105 mole) in 50 ml CH2Cl2 was added, followed by S-2-methylbutylamine, 12 ml, 0.1 mole). After stirring at 0° for two hours, the mixture was allowed to warm to 25° over 1.5 hours. The mixture was filtered, and the solvent was removed in vacuo. The residue was dissolved in EtOAc, which was washed with 1N citric acid, brine, saturated NaHCO3 solution, and brine. The organic phase was dried over MgSO4, filtered, and stripped to a gum, 36.90 g. The gum was dissolved in Et2O and treated with charcoal to remove colored impurities. The suspension was filtered and stripped to a gum, 35.2 g, which was suitable for use in the following procedure without further purification.

STA-MBA

A solution of 38.0 g (0.11 mole) of BOC-STA-MBA in 250 ml CH2Cl2 was treated with HCl gas every one-half hour over a three-hour period. The solvent was removed under reduced pressure and the residue taken up in 30 ml H2O and 110 ml of 1N HCl. The solution was washed twice with Et2O, the pH bought to 13 with 1N NaOH, and the solution extracted twice with Et2O. The Et2O was washed with saturated NaCl, dried, and the solvent removed under reduced pressure, giving 22.3 g of the product as an oil which solidified on standing. The material was sufficiently pure for use in subsequent reactions.

Z-LEU-STA-MBA

A solution of 5.3 g (20.0 mmole) of Z-LEU, 4.89 g (20.0 mmole) of STA-MBA, and 2.76 g (20.4 mmole) of HOBT in 120 ml CH2Cl2 was cooled in ice and 4.21 g (20.4 mmole) of DCC added. After stirring at room temperature overnight, the mixture was filtered, and the filtrate evaporated. The residue was taken up in EtOAc and washed with 1N citric acid, saturated NaCl, saturated NaHCO3, and saturated NaCl. After drying over MgSO4, the solution was reduced to one-third volume, diluted with Et2O, and cooled. The precipitated solid was collected and washed with Et2O, giving 7.93 g of the product as a white solid. The structure was confirmed by NMR and mass spectroscopy

LEU-STA-MBA

A solution of 7.93 g (16.1 mmole) of Z-LEU-STA-MBA in 80 ml MeOH was treated with 0.4 g of 20% Pd/C and the mixture purged with H2 gas for three hours. The mixture was filtered and the filtrate evaporated under reduced pressure to give 5.82 g of the product as a white foam. The structure was confirmed by NMR and mass spectroscopy.

We claim:

1. A peptide of formula

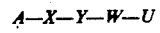

or a pharmaceutically acceptable salt thereof wherein A is IVA or BOC;

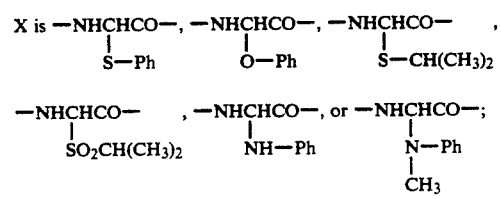

Y is HIS or LEU;
W is CAD or STA; and
U is MBA with the proviso that when W is CAD, U is absent.

2. A peptide selected from the group consisting of:
IVA-NHCH(SPh)CO-HIS-CAD,
IVA-NHCH(SPh)CO-LEU-STA-MBA (Isomer A),
IVA-NHCH(SPh)CO-LEU-STA-MBA (Mixture of diastereomers),
IVA-NHCH(OPh)CO-HIS-CAD,
IVA-NHCH(SCH(CH3)2)CO-HIS-CAD (Isomer A),
IVA-NHCH(SCH(CH3)2)CO-HIS-CAD (Isomer B),
IVA-NHCH(SO2CH(CH3)2)CO-HIS-CAD,
BOC-NHCH(SCH(CH3)2)CO-LEU-STA-MBA,
IVA-NHCH(NHPh)CO-HIS-CAD,
IVA-NHCH(N(CH3)Ph)CO-HIS-CAD, and
IVA-NHCH(NHPh)CO-LEU-STA-MBA.

3. A pharmaceutical composition comprising a renin-inhibitory effective amount of a compound as claimed in claim 1 together with a pharmaceutically acceptable carrier.

4. A method of treating renin-associated hypertension which comprises administering to a mammal a pharmaceutical composition as claimed in claim 3.

5. A pharmaceutical composition comprising a renin associated hyperaldosteronism-inhibitory effective amount of a compound as claimed in claim 1 together with a pharmaceutically acceptable carrier.

6. A method of treating renin associated hyperaldosteronism which comprises administering to a mammal a pharmaceutical composition as claimed in claim 5.

7. A pharmaceutical composition comprising an amount effective for treating renin associated congestive heart failure of a compound as claimed in claim 1 together with a pharmaceutically acceptable carrier.

8. A method of treating renin associated congestive heart failure which comprises administering to a mammal a pharmaceutical composition as claimed in claim 7.

9. A method of determining the presence of renin-associated hypertension in a patient, comprising administering to such a patient, at a hypotensive dosage level and as a single dose, a compound according to claim 1, followed by monitoring of said patient's blood pressure.

* * * * *

UNITED STATES PATENT AND TRADEMARK OFFICE
CERTIFICATE OF CORRECTION

PATENT NO. : 5,221,667
DATED : June 22, 1993
INVENTOR(S) : James S. Kaltenbronn, et al.

It is certified that error appears in the above-indentified patent and that said Letters Patent is hereby corrected as shown below:

Column 24, line 34, delete "CO" and close up space.

Column 24, line 35, insert ")" after subscript "2".

Column 24, line 36, insert ")" after subscript "2".

Column 24, line 37, insert ")" after subscript "2".

Column 24, line 38, insert ")" after subscript "2".

Signed and Sealed this

First Day of February, 1994

*Attest:*

BRUCE LEHMAN

*Attesting Officer*   *Commissioner of Patents and Trademarks*